United States Patent
Takahashi et al.

(10) Patent No.: US 6,489,111 B1
(45) Date of Patent: Dec. 3, 2002

(54) APPARATUS AND METHODS FOR IMMOBILIZED DNA LIBRARY PREPARATION AND GENE AMPLIFICATION

(75) Inventors: Kojiro Takahashi, Hiroshima-ken (JP); Michifumi Tanga, Yamaguchi-ken (JP)

(73) Assignee: Toyo Kohan Co., Ltd., Tokyo (JP)

( * ) Notice: Subject to any disclaimer, the term of this patent is extended or adjusted under 35 U.S.C. 154(b) by 0 days.

(21) Appl. No.: 09/601,973

(22) PCT Filed: Feb. 8, 1999

(86) PCT No.: PCT/JP99/00525

§ 371 (c)(1),
(2), (4) Date: Oct. 12, 2000

(87) PCT Pub. No.: WO99/41362

PCT Pub. Date: Aug. 19, 1999

(30) Foreign Application Priority Data

Feb. 10, 1998 (JP) .............................................. 10-42971

(51) Int. Cl.[7] .......................... C12Q 1/68; C12N 11/16; G01N 15/06; C07H 21/04
(52) U.S. Cl. .......................... 435/6; 435/91.1; 435/91.2; 435/283.1; 435/287.2; 435/288.4; 422/68.1; 536/23.1
(58) Field of Search .............................. 422/68.1; 435/6, 435/287.2, 288.4, 283.1, 91.1, 91.2; 536/23.1

(56) References Cited

U.S. PATENT DOCUMENTS

| | | | | |
|---|---|---|---|---|
| 5,082,935 A | * | 1/1992 | Cruickshank | ............... 536/27 |
| 5,443,791 A | * | 8/1995 | Cathcart et al. | ............... 422/65 |
| 5,605,662 A | * | 2/1997 | Heller et al. | ............... 422/68.1 |
| 5,656,493 A | * | 8/1997 | Mullis et al. | ............. 435/286.1 |
| 5,777,372 A | * | 7/1998 | Kobashi | ...................... 257/414 |
| 6,004,513 A | * | 12/1999 | Albagli et al. | .................. 435/6 |
| 6,043,080 A | * | 3/2000 | Lipshutz et al. | ......... 435/287.2 |
| 6,210,882 B1 | * | 4/2001 | Landers et al. | ................. 435/6 |

OTHER PUBLICATIONS

Shoffner et al. "Chip PCR. 1. Surface passivation of microfabricated silicon–glass chips for PCR" Nucleic Acid Research, 1996, 24(2):375–379.*

Lamture, J. et al. "Direct Detection of Nucleic Acid Hybridization On the Surface of a Charge Coupled Device," Nucleic Acids Research (1994), vol. 22, No. 11, p. 2121–2125.

* cited by examiner

Primary Examiner—W. Gary Jones
Assistant Examiner—B J Forman
(74) Attorney, Agent, or Firm—Browdy and Neimark, P.L.L.C.

(57) ABSTRACT

A purpose of the present invention is to provide a gene amplification apparatus with simple operation, wherein the apparatus can heat and cool gene rapidly and a thermal cycle can be operated in a relatively short period and a method thereof, a method for preparing immobilized DNA library suitable to the above apparatus and a method for comparing genes systematically. The apparatus for preparing immobilized DNA library according to the present invention comprises a reaction body 10 on which a grooved portion for receiving a container is formed, a cap portion 50 provided at an upper portion of the reaction body and a container 12 formed by substrates for immobilizing DNA, wherein the cap portion 50 including means for heating/cooling 51 and means for cooling 52.

15 Claims, 8 Drawing Sheets

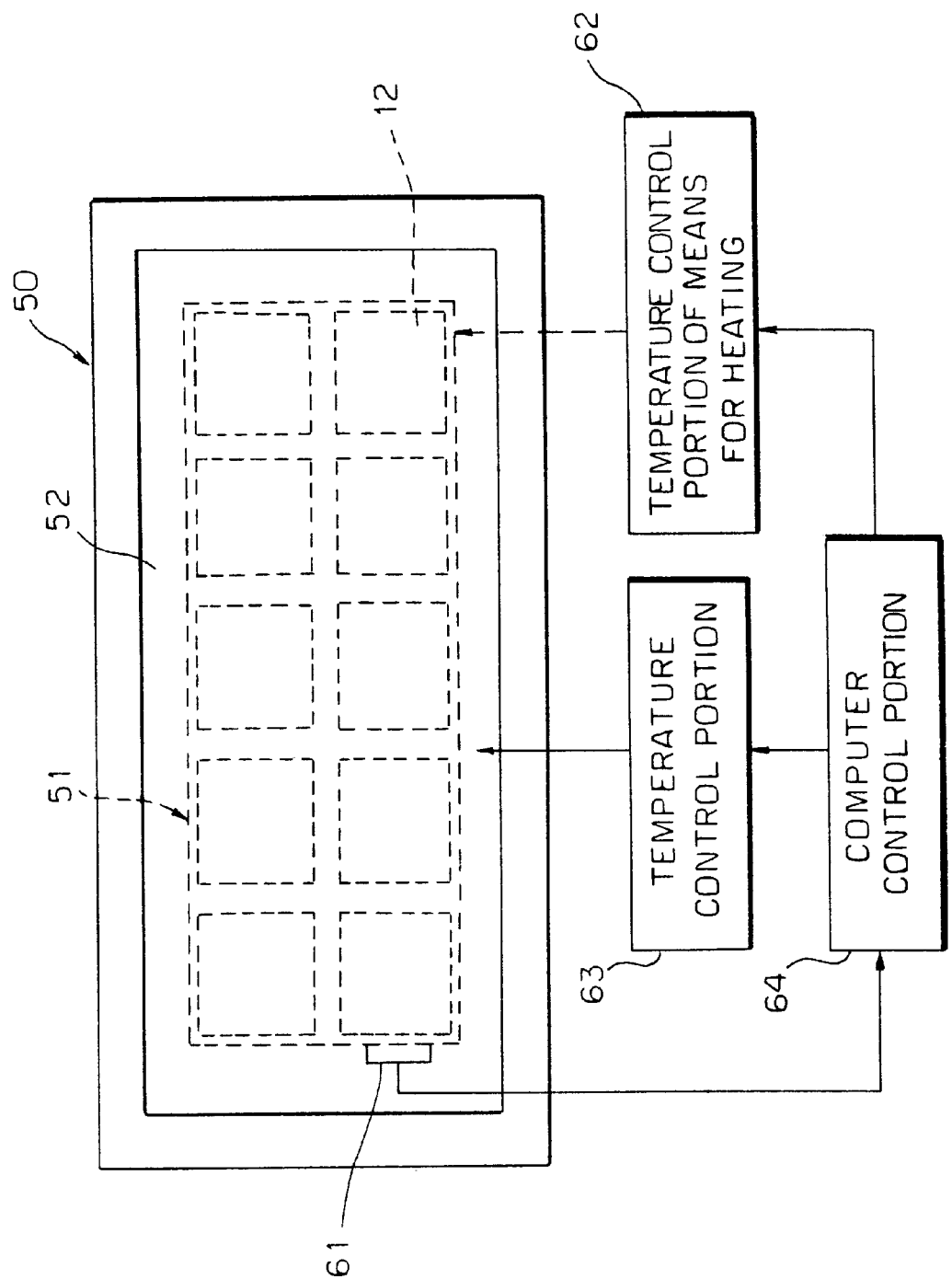

FIG.7A

I. In the case of RT-PCR with mRNA

Oligo-d-A3dT 16-20:AAATTTTT---TTTT   or   Oligo-dC3dT 16-20:CCCTTTTT---TTTTT

[Immobilization (I -I)]:ADC-R-dA3dT16-20
    ADC-R-AAATTTTT---TTTTT      (R: -(CH$_2$)3-COO)

[Hybridization (I -2)]:ADC-R-dA3dT16-20-mRNA      (SEQ ID NO:1)
    ADC-R-AAATTTTT---TTTTT
    AAA---AAAAAGTCAGCCATA--GTCA-(3'-mRNA-5')-GGCACAGT--AATCCG---

[RT (I -3)]:ADC-R-dA3dT 16-20-cDNA-mRNA
    ADC-R-AAATTTTT---TTTTTCAGTCGGTAT--CAGT-(3'-cDNA-5')-CCGTGTCA--TTAGGC---
    AAA----AAAAAGTCAGCCATA--GTCA-(3'-mRNA-5')-GGCACAGT--AATCCG---

[Dehybridization (I -3)]:ADC-R-dA3dT16-20-cDNA(Immobilized DNA library)
    ADC-R-AAATTTTT---TTTTTCAGTCGGTAT--CAGT-(3'-cDNA-5')-CCGTGTCA--TTAGGC---

[PCR (I -4)]:ADC-R-dA3dT 16-20-cDNA, Primers (P3',P5')
    ADC-R-AAATTTTT---TTTTTCAGTCGGTAT--CAGT-(3'-cDNA-5')-CCGTGTCA--TTAGGC---
    (P3':GCCATA--GT)           (P5':TGTCA--TTA)

FIG. 7B

1st Cycle:

```
                                    GCCATA--GTCA----------GGCACAGT--AATCCG---
ADC-R-AAATTTTT----TTTTTCAGTCGGTAT--CAGT-(3'-cDNA-5')-CCGTGTCA--TTAGGC----
```

2nd Cycle:

```
                                    GCCATA-GTCA----------GGCACAGT--AATCCG---
                                    CGGTAT-CAGT----------TGTCA-TTA
                                    GCCATA-GTCA----------GGCACAGT--AATCCG---
ADC-R-AAA-TTTTT---TTTTTCAGTCGGTAT--CAGT-(3'--cDNA-5')-CCGTGTCA--TTAGGC---
```

3rd Cycle

```
                                    GCCATA--GTCA----------GGCACAGT--AATCCG---
                                    CGGTAT--CAGT----------TGTCA-TTA
                                    GCCATA--GTCA----------GGCACAGT--AAT
                                    CGGTAT--CAGT----------TGTCA-TTA
                                    GCCATA--GTCA----------GGCACAGT--AATCCG---
                                    GCCATA--GTCA----------GGCACAGT--AAT
                                    GCCATA--GTCA----------GGCACAGT--AATCCG---
ADC-R-AAA-TTTTT-TTTTTCAGTCGGTAT--CAGT-(3'--cDNA-5')-CCGTGTCA--TTAGGC---
```

FIG. 8A

II. In the case of PCR with gDNA

BamHI: (side of immobilization)  AAA (T/G)5-10<u>GGATCC</u>(T/G)2-5    (SEQ ID No:2)
       (side of hybridization)   TTT (A/C)5-10<u>CCTAGG</u>(A/C)2-5

EcoRI: (side of immobilization)  AAAGG(T/G)5-8<u>GAATTC</u>(T/G)2-5   (SEQ ID No:3)
       (side of hybridization)   TTTCC(a/C)5-8<u>CTTAAG</u>(A/C)2-5

[Immobilization (II-1)]:
    ADC-R-AAA (T/G) 5-10<u>GGATCC</u> (T/G)2-5

[Hybridization (II-2)]:
    ADC-R-AAA (T/G) 5-10<u>GGATCC</u> (T/G)2-5
              TTT(A/C)5-10<u>CCTAGG</u>(A/C)2-5

[Cutting the restricted enzyme (II-3)]:
    ADSC-R-AAA (T/G)5-10<u>G</u>
               TTT(A/C)5-10<u>CCTAG</u>

[Ligase(II-4)]:
ADC-R-AAA(T/G)5-10<u>GGATCC</u>ATGGCCTTACGCGT-AACCGTTAGAG---ATGC-GTACCATG-   (SEQ ID NO:4)
TTT(A/C)5-10<u>CCTAG</u> GTACCGGAATGCGCA-TTGGCAATCATC---TACG-CATGGTAC- ADC-R-AAA(T/G)5-10<u>GGATCC</u>ATGGCCTTACGCGT--AACCGTTAGAG---ATGC-GTACCATG--   (SEQ ID NO:5)
TTT(A/C)5-10<u>CCTAGG</u>TACCGGAATGCGCA--TTGGCAATCATC---TACG--CATGGTAC--

FIG. 8B

[PCR (II -5)]:ADSC-Oligo-restricted enzyme portion -gDNA (g-DNA Library), Primers(P5',P3')

P5':GCGT--AACCGT)

ADC-R-AAA(T/G)5-10GGATCCATGGCCTTACGCGT--AACCGTTAGAG----ATGC--GTACCATG-

TTT(A/C)5-10CCTAGGTACCGGAATGCGCA--TTGGCAATCATC----TACG--CATGGTAC--

(P3':ACG--CATGGT)

1st Cycle:

-T(A/C)5-10CCTAGGTACCGGAATGCGCA--TTGGCAATCATC----TACG--CATGGT

ADC-R-AAA(T/G)5-10GGATCCATGGCCTTACGCGT--AACCGTTAGTAG----ATGC--GTACCATG-

GCGT--AACCGTTAGTAG----ATGC--GTACCATG--

TTT(A/C)5-10CCTAGGTACCGGAATGCGCA--TTGGCAATCATC----TACG--CATGGTAC--

2nd Cycle:

GCGT--AACCGTTAGTAG----ATGC--GTACCA

-T(A/C)5-10CCTAGGTACCGGAATGCGCA--TTGGCAATCATC----TACG--CATGGT

ADC-R-AAA(T/G)5-10GGATCCATGGCCTTACGCGT--AACCGTTAGTAG----ATGC--GTACCATG--

-T(A/C)5-10CCTAGGTACCGGAATGCGCA--TTGGCAATCATC----TACG--CATGGT

GCGT---AACCGTTAGTAG----ATGC--GTACCA

GCGT---AACCGTTAGTAG----ATGC--GTACCATG--

GCGT---AACCGTTAGTAG----ATGC--GTACCATG--

TTT(A/C)5-10CCTAGGTACCGGAATGCGCA---TTGGCAATCATC----TACG--CATGGTAC--

US 6,489,111 B1

APPARATUS AND METHODS FOR IMMOBILIZED DNA LIBRARY PREPARATION AND GENE AMPLIFICATION

CROSS REFERENCE TO RELATED APPLICATION

The present application is the national stage under 35 U.S.C. 371 of PCT/JP99/00525, filed Feb. 8, 1999.

FIELD OF THE INVENTION

The present invention relates to a reaction apparatus which can be used for a variety of reactions by heating a small amount of solution. Particularly, the present invention relates to a method for immobilized DNA library preparation, a method for gene amplification, a method for comparing genes systematically, an apparatus therefor and immobilized DNA library therefore.

BACKGROUND OF THE INVENTION

Conventionally, a polymerase-chain-reaction (PCR) method has been broadly utilized as means for amplifying genes. In the PCR method, a tube-shaped plastic reaction container which is filled with reaction solution is inserted into an aluminium block and so on with a cap for preventing the reaction solution from evaporating. The temperature of the aluminium block is periodically changed to a thermal metamorphic temperature, an annealing temperature and a DNA synthetic temperature in order. Such a thermal control cycle is repeated for a predetermined number of times.

However, in the conventional PCR method, the device used is a plastic reaction container which has relatively high thermal capacity and relatively low thermal conductivity. Further, the thermal control is operated with respect to an aluminium block itself. Therefore, a long time is required for heating/cooling. A target duplicated amount of DNA is relatively low, since thermal control of the reaction solution is not operated completely.

A purpose of the present invention is to resolve the above drawbacks and to provide an apparatus for gene amplification having simple operation wherein a step of heating/cooling can be operated rapidly and a thermal cycle of the reaction can be shortened. Another object of the present invention is to provide a method for amplifying genes.

Another purpose of the present invention is to provide a method for comparing genes systematically using the above apparatus.

SUMMARY OF THE INVENTION

An apparatus for preparing immobilized DNA library according to the present invention is an apparatus comprising a reaction body on which a groove portion for receiving a container is provided and a cap portion provided at an upper portion of the reaction body with means for heating/cooling and means for cooling, wherein the apparatus is characterized in that the container is made of at least one substrate which has been chemically modified.

A gene amplifying apparatus according to the present invention is an apparatus comprising a reaction body on which a groove portion for receiving a container is formed. A cap portion is provided at an upper portion of the reaction body with means for heating/cooling and means for cooling, wherein the apparatus is characterized in that the container is made of at least one substrate for immobilizing genes. In these apparatus, it is preferable that the substrates are solid-state substrates and the container is a separable type and a cassette type.

In a method for temperature control by the apparatus for amplifying genes according to the present invention, the method is characterized that a signal from a temperature measuring portion 61 is input to a computer control portion 64 and the computer control portion 64 compares the information input the signals and program chart previously input so that a thermal control portion 62 of means for heating/cooling 51 and a thermal control portion 63 of means for cooling 52 can be driven.

In a method for temperature control by the apparatus for amplifying genes according to the present invention, the method is characterized that a signal from a temperature measuring portion 61 is input to a computer control portion 64 and the computer control portion 64 compares with the signals and program chart previously input so that a thermal control portion 62 of means for heating/cooling 51 and a thermal control portion 63 of means for cooling 52 can be driven.

The substrates for immobilizing DNA according to the present invention are characterized in that the substrates are utilized in the above apparatuses.

A method for preserving the substrates in a refrigerator according to the present invention is characterized in that the substrates for immobilizing DNA is preserved in the refrigerator.

A method for comparing genes systematically according to the present invention is characterized in that a plurality of DNA-immobilized libraries are set in a container.

BRIEF DESCRIPTION OF THE DRAWINGS

FIG. 6 shows a process for controlling the temperature of the gene amplifying apparatus according to the present invention.

FIG. 7 shows a process for producing an immobilized cDNA library and for gene amplification. The sequence presented in "[Hybridization (I-2)]" as 5'-ATACCGACTGAAAAA-3' is designated as SEQ ID NO:1.

FIG. 8 shows a process for producing an immobilized gDNA library and for gene amplification. The sequence presented as "BamHI: (side of immobilization)" is designated as SEQ ID NO:2; the sequence presented as "EcoRI: (side of immobilization)" is designated as SEQ ID NO:3; and the sequences presented in the top line of "[Ligase (II-4)]" are designated as SEQ ID NOs:4 and 5.

BEST MODE FOR CARRYING OUT THE INVENTION

A gene amplification apparatus according to the present invention will be described.

Figure 1:
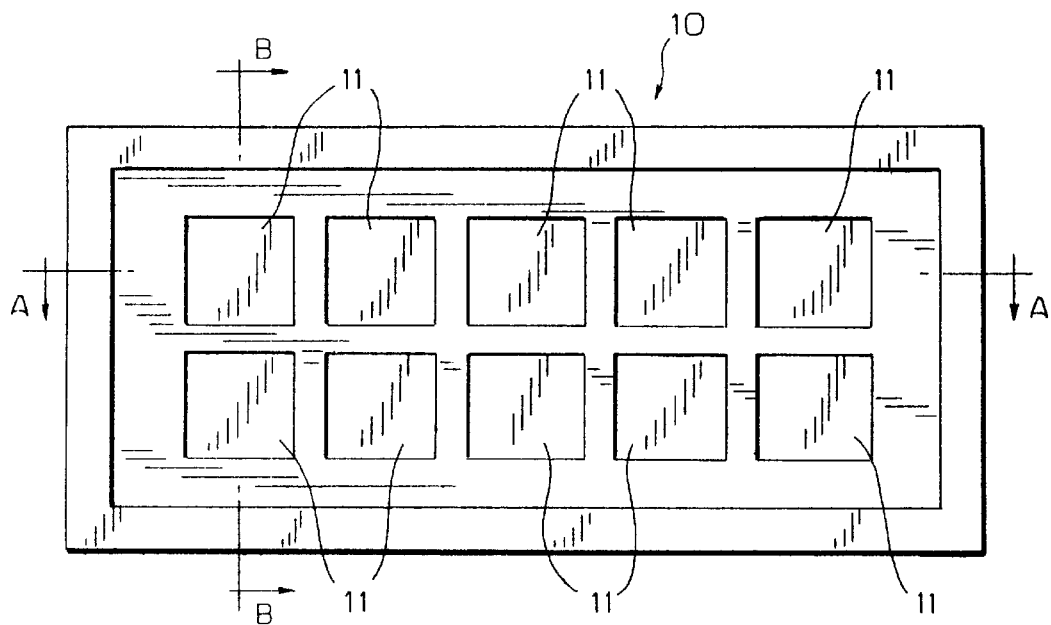
FIG. 1 shows a plan view of a gene amplifying apparatus according to the present invention, wherein a cap is opened.
Figure 2:
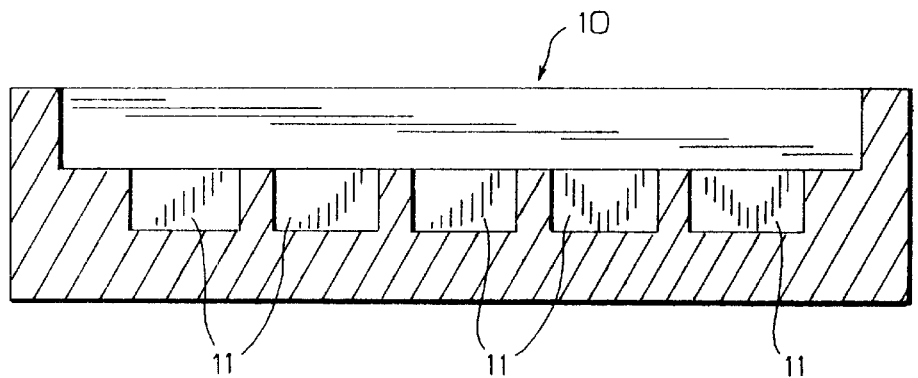
FIG. 2 shows a cross sectional view taken a line A—A in FIG. 1.
Figure 3:
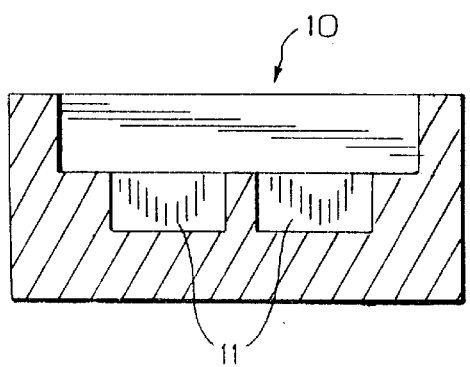
FIG. 3 shows a cross sectional view taken a line B—B in FIG. 1.

FIG. 1 shows a plane view of the gene amplification apparatus according to the present invention, wherein a cap is opened. FIG. 2 shows a cross sectional view of the gene amplification apparatus according to the present invention taken a line A—A in FIG. 1. FIG. 3 shows a cross sectional view of the apparatus taken along a line B—B in FIG. 1. FIG. 4 shows a process how to make a container. FIG. 5 shows a cross sectional view of the gene amplification apparatus according to the present invention.

As shown in FIG. 1 to FIG. 3, numeral 10 indicates a reaction body and numeral 11 indicates a grooved portion formed on the reaction body. It is preferable that the reaction body 10 is made of chemically stable polymer material such as acrylic resin and polystyrene resin. At least one grooved portion 11 is formed on the reaction body. The shape of the grooved portion is preferably cylindrical or a polygonal pole such as a triangular pole or a square pole. It is preferable that a container 12 is made of a diamond substrate, a ceramic substrate such as an aluminum nitride substrate and a silicone carbide substrate and a metallic substrate such as an aluminum substrate and a stainless steel substrate.

Alternatively, it is preferably a diamond-like carbon substrate of which a part is made of diamond, a carbon substrate and a carbon compound substrate. It is also preferably a plastic substrate such as a polycarbonate substrate and a fluorocarbon substrate. Further, it is preferably a substrate combined with the above described substrates.

The container 12 may have a bottom portion and is preferably attached to/detached from the grooved portion 11 easily.

Figure 4A:
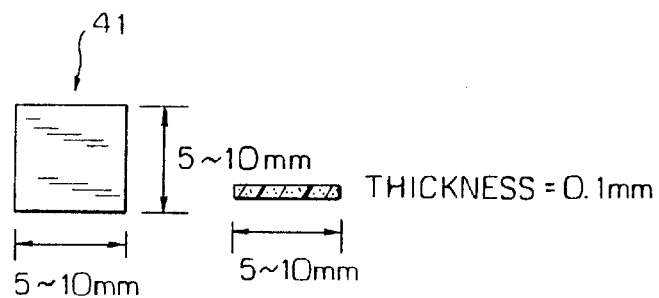
FIG. 4 shows a process for making a container.
Figure 4B:
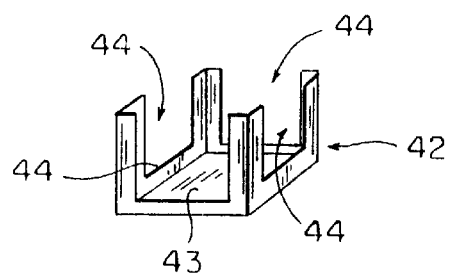
Figure 4C:
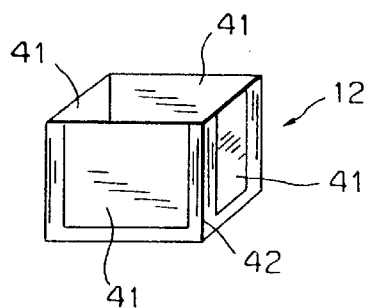

The container 12 preferably comprises substrates divided into a bottom portion and side wall portions. For example, in the case of a square pole container, the substrates can be divided to a bottom wall portion and four side wall portions. As shown in FIG. 4(a), each edge of the respective substrate is from 5 mm to 10 mm and a thickness of the each substrate is about 0.1 mm. As shown in FIG. 4(b), a container 12 may be assembled by a bottom portion 43 and side wall portions 44 with a synthetic resin substrate holder 42 (see FIG. 4(c)).

In such a case, it is preferable that the container comprises a bottom portion or at least one side wall portion, wherein genes are immobilized on at least one substrate of the portion.

Further, these containers 12 may be connected with each other (cassette type) so that a plurality of containers can be attached to/detached from a plurality of grooved portions 11 in one action so as to improve operating efficiency. A detailed description of the cassette type containers will be described at a description of immobilized DNA library.

Figure 5A:
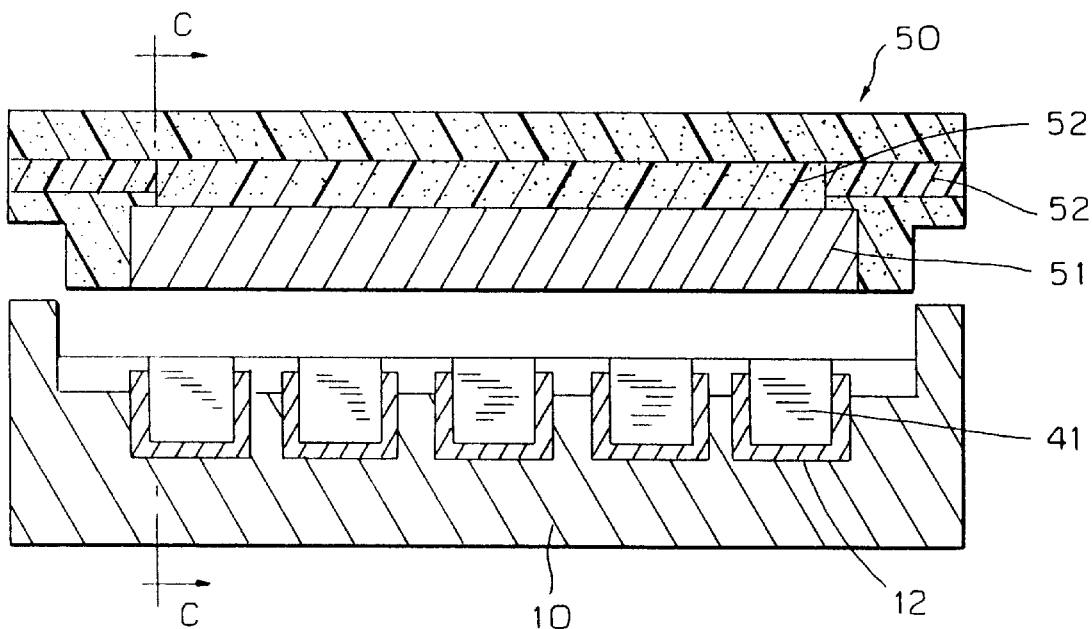
Figure 5B:
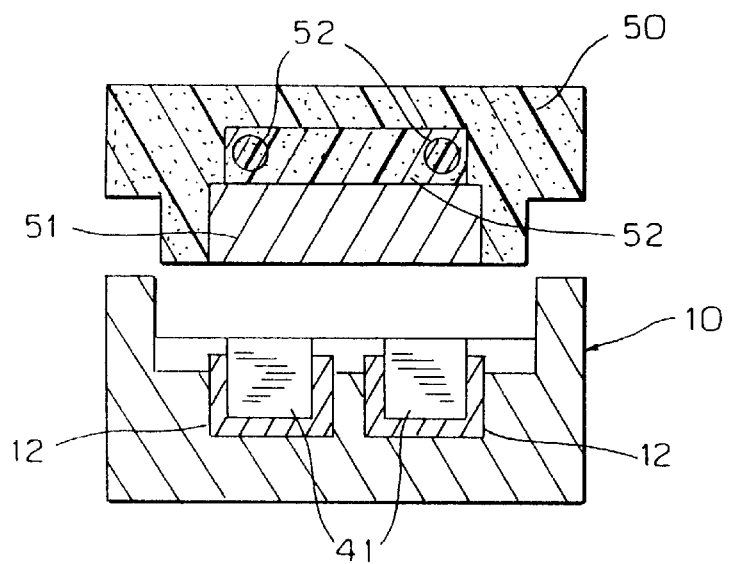

FIG. 5 shows a cross sectional view of a gene amplification apparatus according to the present invention. FIG. 5(a) shows a reaction container 10 with a cap portion 50 mounted on an upper portion of the reaction container 10. FIG. 5(b) shows a cross sectional view taken a line C—C in FIG. 5(a). In FIG. 5, numerals 50, 51 and 52 indicates a cap portion, means for heating/cooling and means for cooling, respectively. It is preferable that the cap portion is made of chemically stable polymeric material such as acrylic resin, polystyrene resin and etc.

Means for heating/cooling 51 is means for heating/cooling the container 12 by contacting the container 12. It is preferable that means for heating/cooling 51 is a Peltier element, an electrical heater, an infrared lamp and so on. By directly contacting the container 12, the temperature of the container 12 can be directly controlled. In comparison with a conventional amplification apparatus the thermal control accuracy of the apparatus of the present invention is superior. Means for cooling 52 is a unit comprising a pipe into which coolant or cool air is directed or a cooling fan is used so as to cool the container 12 rapidly. FIG. 6 shows a thermal control unit of a gene amplification apparatus according to the present invention. In FIG. 6, the temperature of the container 12 is controlled by a temperature control portion 62 of means for heating/cooling 51 and a thermal control portion 63 of means for cooling 62 in accordance with information from a temperature measuring portion 61. A signal from the temperature measuring portion 61 that is directly contacted with a bottom portion or side wall portion of the container 12 is input to a computer control portion 64. The computer control portion 64 compares the input signal and a program chart (temperature increasing speed, maintained temperature, maintained time, temperature decreasing speed, and so on) previously input. As the result, the temperature control portion 62 of means for heating/cooling 51 and the temperature control portion 63 of means for cooling 52 can be driven.

EMBODIMENTS

Embodiments according to the present invention will be described with reference to FIG. 7 and FIG. 8. As a container 12, diamond chips 41 (5 mm×5 mm, thickness 0.1 mm) are utilized as diamond substrates. As shown in FIG. 4, one diamond chip is utilized as a bottom portion and four diamond chips are utilized as side wall portions. These diamond chips are assembled with a synthetic resin substrate holder 42 so as to form a container 12. The diamond chips 41 utilized as the side wall portions are chemically modified with organic carbonic acid. After assembling the container 12, the cap portion 50 is mounted on an upper portion of the reaction body 10.

Preparing Immobilized DNA Library

Next, an example of preparing immobilized DNA library will be described with reference to FIG. 7 and FIG. 8. At first, in the case of mRNA (messenger RNA), oligo $dT_{16-20}$ are immobilized on the surfaces of the four diamond chips 41 contacting the solution in the container 12 by a chemical ester linkage reaction. In the case of gDNA (genomic DNA), oligonucleotides having restricted enzyme portions are immobilized on the surface of the diamond chips 41 by a chemical ester linkage reaction. The four diamond chips 41 have been chemically modified with organic carbonic acid. In order to immobilize, a 3' terminal of the oligo $dT_{16-20}$ and a 5' terminal of the oligonucleotide are requested to connect with adenine (A) or cytosine (C) or guanine (G) which comprises amino radical. In FIG. 7 and FIG. 8, a mark "ADC-R-" indicates a diamond chip chemically modified with organic carbonic acid.

Next, in the case of cDNA (complementary DNA), the total RNA solution containing mRNA is extracted from tissues and cells, and mRNA is hybridized with oligo-$dT_{16-20}$ at a low temperature of 0° C. to 4° C. After hybridization, cDNA is synthesized by Reverse Transcriptase (RT) at a suitable constant temperature of 37° C. to 60° C. The cDNA are reacted and immobilized so as to extend toward the terminal 5' of hybridized oligo-$dT_{16-20}$. Hybridized solution of synthesized immobilized cDNA and mRNA is heated up to 90° C. in order to dehybridize mRNA. Then, the reaction solution is exchanged to Tris-EDTA (TE) buffer solution. The reaction solution is cleaned with ethanol at a low temperature of 0° C. to 4° C. again. Thus, a purified immobilized cDNA library in one chain DNA condition is prepared (see FIG. 7).

In the case of gDNA library, immobilized oligonucelotides target restrictive enzymes (see. FIG. 8) are immobilized on surfaces of the diamond chips 41 as for oligo-$dT_{16-20}$. Next, for chemical immobilization, the reaction solution is exchanged for reaction solution including hybridized oligonucleotides with target restrictive enzymes at a low temperature of 0° C. to 4° C. After hybridization with oligonucleotides, the reaction solution is heated to 37° C. so as to cut the restrictive enzymes of the semi-immobilized oligonucleotides.

After cutting the restrictive enzyme, the reaction container is cooled down at a low temperature of 0° C. to 4° C. again. The reaction solution is exchanged for reaction solution including gDNA of which target restrictive enzyme is cut and Ligase enzyme. The exchanged solution is heated up to 37° C. again so as to effect a Ligase reaction. As a result, a gDNA library in one chain DNA condition can be prepared (see FIG. 8).

Immobilized cDNA library prepared on surfaces of the diamond chips or immobilized gDNA library prepared on the surfaces of the diamond chips can be set in the different containers so as to compare systematically for the purposes (1) to (3).

(1) To compare gene variation of the same kind of tissues and cells of the plurality of samples.
(2) To compare gene production and variation of each tissue and cell of the same sample.
(3) To compare gene production and variation of the original genes and genes after medical treatment, sergeant and so on with respect to the same sample.

For example, in the case of (1), the plurality of samples (a plurality of diamond chips having immobilized DNA library) are set in different containers so as to compare gene variation of the same kind of tissues and cells. These pluralities of containers are designated as one cassette. These cassettes are attached to a reaction body. If two or more than cassettes are prepared systematically, a plurality of samples can be compared effectively.

In the present invention, one cassette in which a plurality of containers are connected or a plurality of cassettes are set is referred to as an aggregation. An immobilized DNA library is set in each container of the aggregation, which is designated as a cassette type immobilized DNA library. In the present invention, these cassette type immobilized DNA libraries are utilized to compare the above described purposes (1) and (2) systematically so that variation of genes can be searched effectively.

Whether or not the PCR method is utilized, the cassette type immobilized DNA library can be utilized semi-permanently in accordance with the request of the comparison data and so on by sufficiently cleaning the containers with TE buffer solution and ethanol solution (70–75%) and refrigerating and preserving the containers by immersing them in ethanol solution (100%).

Amplifying Genes with Immobilized DNA Library

Side wall portions of the container 12 are formed by cassette type immobilized DNA libraries of the above immobilized cDNA or gDNA. Inner surfaces of the container 12 are sufficiently cleaned with TE buffer solution. Then, a primer with respect to amplified DNA is set and PCR reaction solution including four kind of nucleotide and DNA polymerase is added. After adding the solution, the container 12 is thermally changed to a thermal metamorphic temperature for dividing two chain DNA into one chain DNA (95° C., about 1.5 minute), an annealing temperature for connecting the one chain DNA and DNA primer (45° C., about 1 minute) and a DNA amplification temperature for extending DNA chain by heat-resistant DNA polymerase (74° C., about 2 minute) in order. This thermal control is repeated 30 times in order to operate the PCR method (see FIG. 7 and FIG. 8). In order to search genes of a plurality of samples at once for a relatively short time, it may provide a system in which the necessary number of apparatuses for preparing the cassette type immobilized DNA library and amplifying genes are juxtaposed. For example, in the case of 50 samples, five apparatuses for amplifying genes according to the present invention may be juxtaposed.

The apparatus according to the present invention can heat and cool reaction solution in a reaction container rapidly so that DNA can be amplified remarkably short time. The apparatus according to the present invention can be used for an automatic gene diagnosis apparatus. In development of the automatic gene diagnosis apparatus, the most important technical problems are a preparation of a cassette type immobilized library utilized semi-permanently and a development of a gene amplification apparatus having excellent efficiency and specificity in view of gene amplification.

Both described problems can be resolved by providing a high performance automatic cassette type immobilized DNA library and a gene amplification apparatus with the most simple operation and the most compact size, so that thermal control from a step of preparation of the library in the PCT method can be controlled by the same substrates.

That is, in accordance with an apparatus according to the present invention, thermal control for amplifying genes can be directly controlled by utilizing diamond chips immobilized DNA library in addition to thermal control for directly controlling DNA immobilized reaction. In accordance with an apparatus according to the present invention, thermal control for PCR reaction solution can be directly controlled by utilizing substrates such as high conductivity diamond substrates so that thermal control efficiency of the PCR method can be remarkably improved and the necessary time can be remarkably shortened. In addition, the PCR efficiency such as specifically amplification of target DNA can be improved.

If the substrate according to the present invention are of high conductivity, a prepared immobilized DNA library becomes very stable, since the diamond substrates are stable with respect to chemical material/solution, excellent in view of heat-resistant and strong with respect to radiation exposure. Once a cassette type immobilized DNA library is prepared, it is possible to provide a DNA library repeatedly utilized for semi-permanent.

By utilizing the high conductivity of diamond substrates, DNA-immobilized chips having DNA immobilized on diamond substrates without being chemically modified may be set in an amplification apparatus according to the present invention so as to operate in a conventional PCR method.

What is claimed is:

1. An apparatus for preparing an immobilized DNA library comprising:
   a reaction body on which a grooved portion having positioned therein a container comprising a synthetic resin holder and five substrates assembled in a bottom portion and four side wall portions is formed, and
   a cap portion provided at an upper portion of said reaction body, said cap portion including a Peltier element system for heating and cooling and including a means for cooling,
   wherein said substrates are selected from the group consisting of aluminum nitride, silicon carbide, stainless steel, and diamond-like carbon wherein said diamond-like carbon substrate is chemically modified by organic carbonic acid.

2. An apparatus as claimed in claim 1 wherein said container is a cassette.

3. A substrate for immobilizing DNA in the apparatus as claimed in claim 1 wherein said substrate is selected from the group consisting of aluminum nitride, silicon carbide, stainless steel, and diamond-like carbon wherein said diamond like carbon is chemically modified by organic carbonic acid.

4. A method for preparing an immobilized DNA library comprising:
   a. immobilizing DNA to be used in the DNA library on five substrates chemically modified by organic carbonic acid in an apparatus according to claim 1;
   b. hybridizing messenger RNA with the immobilized DNA comprising oligo-dA$_3$T$_{16-20}$;
   c. amplifying complementary DNA on a side of the immobilized DNA;
   d. heating and cooling the apparatus by inputting a signal from a temperature measuring portion directly in contact with the five substrates assembled on a bottom portion or four side wall portions of said container;
   e. comparing a previously introduced input signal and program chart with the conditions in the apparatus; and
   f. driving a temperature control portion of a Peltier element system for heating and cooling and then driving a temperature control portion of a means for cooling.

5. A method for preparing an immobilized DNA library using an apparatus as claimed in claim 1 comprising:
   a. imputing a signal from a temperature measuring portion which is directly in contact with five substrates assembled in a bottom portion or four side wall portions of a container to a computer control portion;
   b. comparing the input signal and a program chart using the computer control portion, wherein the program chart comprises speed of increasing temperature, temperature maintained, time temperature is maintained, speed of decreasing temperature previously input; and
   c. driving a temperature control portion of a Peltier element system for heating and cooling and a temperature control portion of a cooling means.

6. An apparatus for amplifying genes comprising:
   a reaction body on which a grooved portion having positioned therein a container comprising a synthetic resin holder and five substrates assembled in a bottom portion and four side wall portions is formed, and
   a cap portion provided at an upper portion of said reaction body, said cap portion including a Peltier element system heating and cooling and including a means for cooling, wherein said substrates are selected from the group consisting of aluminum nitride, silicon carbide, stainless steel, and diamond-like carbon wherein said diamond-like carbon substrate is chemically modified by carbonic acid.

7. An apparatus as claimed in claim 6, wherein said substrates are solid-state substrates.

8. The apparatus of claim 6, wherein said container is divided.

9. A method for amplifying genes in an apparatus according to claim 6 comprising:
   a. immobilizing DNA to be used in the DNA library on five substrates chemically modified by organic carbonic acid in an apparatus according to claim 1;
   b. hybridizing messenger RNA with the immobilized DNA comprising oligo-dA$_3$T$_{16-20}$;
   c. amplifying complementary DNA on a side of the immobilized DNA comprising oligo-dA$_3$T$_{16-20}$;
   f. heating and cooling the apparatus comprising inputting a signal from a temperature measuring portion directly in contact with the five substrates assembled on a bottom portion or four side wall portions of said container;
   g. comparing a previously introduced input signal and program chart with the conditions in the apparatus; and
   h. driving a temperature control portion of a Piltier element for heating and cooling and then driving a temperature control portion of a means for cooling.

10. A method for amplifying genes using an apparatus according to claim 6 comprising:
    a. inputting a signal to a computer control portion from a temperature measuring portion which is in direct contact with five substrates assembled on a bottom portion or on four side wall portions of a container;
    b. comparing the input signal in the computer control portion with a program chart, wherein said program chart comprises speed of increasing temperature, maintained temperature, maintained time, and speed of decreasing temperature which have been input previously; and
    c. driving a temperature control portion of a Peltier element system for heating and cooling and a temperature control portion of a cooling means.

11. An apparatus for amplifying genes comprising:
    a reaction body on which a grooved portion having positioned therein a container comprising a synthetic resin holder and five substrates assembled in a bottom portion and four side wall portions is formed, and
    a cap portion provided at an upper portion of said reaction body, said cap portion including a Peltier element system for heating and cooling and including a means for cooling,
    wherein said container substrates are selected from the group consisting of aluminum nitride, silicon carbide, stainless steel, and diamond-like carbon wherein said diamond-like carbon substrate is chemically modified by organic carbonic acid.

12. A method for amplifying genes in an apparatus according to claim 11 comprising:
    a. immobilizing DNA to be used in the DNA library on five substrates chemically modified by organic carbonic acid in an apparatus according to claim 1;
    b. hybridizing messenger RNA with the immobilized DNA comprising oligo-dA$_3$T$_{16-20}$;
    c. amplifying complimentary DNA on a side of the immobilized DNA comprising oligo-dA$_3$T$_{16-20}$;

d. heating and cooling the apparatus by inputting a signal from a temperature measuring portion directly in contact with five substrates assembled in a bottom portion or four side wall portions of said container;

e. comparing a previously introduced input signal and program chart with the conditions in the apparatus; and f. driving a temperature control portion of a Peltier element for heating and cooling and then driving a temperature control portion of a means for cooling.

13. A method for amplifying genes using an apparatus as claimed in claim 11 comprising:

a. inputting a signal to a computer control portion from a temperature measuring portion which is in direct contact with five substrates assembled on a bottom portion or on four side wall portions of a container;

b. comparing the input signal in the computer control portion with a program chart, wherein said program chart comprises speed of increasing temperature, maintained temperature, maintained time, and speed of decreasing temperature which have been input previously; and c. driving a temperature control portion of a Peltier element system for heating and cooling and a temperature control portion of a cooling means.

14. A method for pretreatment in refrigerating and preserving substrates for immobilizing DNA comprising oligo-$dA_3T_{16-20}$, in an apparatus said method comprising:

a. cleaning said substrates with a solution containing tris-ethylene diamine tetraacetic acid buffer solution and 70–75% ethanol solution;

b. immersing said substrates in 100% ethanol;

c. refrigerating and preserving said ethanol containing said substrate; and d. positioning said substrate into the container of an apparatus according to claim 1.

15. A method for refrigerating and preserving substrates for immobilizing DNA in a apparatus consisting of the following steps:

a. immobilizing DNA on five substrates which have been chemically modified by an organic carbonic acid;

b. cleaning the substrates with a solution containing tris-ethylene-diamine tetraacetic acid buffer solution and 70–75% ethanol solution;

c. immersing the substrates in 100% ethanol;

d. refrigerating and preserving said substrates in 100% ethanol; and e. positioning said substrate into the container of an apparatus according to claim 1.

* * * * *

SEQUENCE LISTING

<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: synthetic

<400> SEQUENCE: 1
ataccgactg aaaaa                                                        15

<210> SEQ ID NO 2
<211> LENGTH: 24
<212> TYPE: DNA
<213> ORGANISM: Artificial Sequence
<220> FEATURE:
<223> OTHER INFORMATION: synthetic
<221> NAME/KEY: misc_feature
<222> LOCATION: (9)..(13)
<223> OTHER INFORMATION: The nucleotides at positions 9-13 can be
      present or absent.

<400> SEQUENCE: 2
aaakkkkkkk kkkggatcck kkkk                                              24

<210> SEQ ID NO 3
<211> LENGTH: 24
<212> TYPE: DNA
<213> ORGANISM: Artificial Sequence
<220> FEATURE:
<223> OTHER INFORMATION: synthetic
<221> NAME/KEY: misc_feature
<222> LOCATION: (11)..(13)
<223> OTHER INFORMATION: The nucleotides at positions 11-13 can be
      present or absent.

<400> SEQUENCE: 3
aaaggkkkkk kkkgaattck kkkk                                              24

<210> SEQ ID NO 4
<211> LENGTH: 33
<212> TYPE: DNA
<213> ORGANISM: Artificial Sequence
<220> FEATURE:
<223> OTHER INFORMATION: synthetic
<221> NAME/KEY: misc_feature
<222> LOCATION: (9)..(13)
<223> OTHER INFORMATION: The nucleotides at positions 9-13 can be
      present or absent.

<400> SEQUENCE: 4
aaakkkkkkk kkkggatcca tggccttacg cgt                                    33

<210> SEQ ID NO 5
<211> LENGTH: 11
<212> TYPE: DNA
<213> ORGANISM: Artificial Sequence
<220> FEATURE:
<223> OTHER INFORMATION: synthetic

<400> SEQUENCE: 5
aaccgttaga g                                                            11